United States Patent [19]

Klein et al.

[11] Patent Number: 5,039,420

[45] Date of Patent: Aug. 13, 1991

[54] HYDROPHILIC SEMIPERMEABLE MEMBRANES BASED ON COPOLYMERS OF ACRYLONITRILE AND HYDROXYALKYL ESTERS OF (METH) ACRYLIC ACID

[76] Inventors: Elias Klein, 5517 Hempstead Rd., Louisville, Ky. 40207; Lalith K. Silva, 2240 Preston St., Apt. 1, Louisville, Ky. 40217

[21] Appl. No.: 568,041

[22] Filed: Aug. 16, 1990

[51] Int. Cl.$^5$ .............................................. B01D 13/00
[52] U.S. Cl. ..................................... 210/645; 210/650; 210/651; 210/653; 210/500.21; 210/500.27; 210/500.35; 210/500.43
[58] Field of Search ....................... 210/500.35, 500.27, 210/500.43, 500.21, 500.23, 650, 651, 653, 500.28, 645; 525/227; 427/44; 429/249

[56] References Cited

U.S. PATENT DOCUMENTS

| | | | |
|---|---|---|---|
| 3,616,930 | 11/1971 | McClements Muir | 210/500.35 |
| 3,950,257 | 4/1976 | Ishii et al. | 210/500.35 |
| 4,177,150 | 12/1979 | Inoue et al. | 210/500.35 |
| 4,252,652 | 2/1981 | Elfert et al. | 210/500.43 |
| 4,545,910 | 10/1985 | Marze | 210/500.27 |
| 4,749,619 | 6/1988 | Angleraud | 210/500.43 |

*Primary Examiner*—Robert A. Dawson
*Assistant Examiner*—Ana Fortuna
*Attorney, Agent, or Firm*—Hoffman, Wasson & Gitler

[57] ABSTRACT

Hydrophilic semipermeable membranes based on copolymers of acrylonitrile and hydroxy-$C_2$–$C_4$-alkyl esters of (meth)acrylic acid are provided. The membranes have a substantial water regain at equilibrium, a wide range of ultrafiltration rates, and low solute adsorption by ion-exchange or hydrophobic interaction mechanisms. The membranes are particularly suitable for processing protein containing fluids, especially biological fluids such as blood or plasmas.

22 Claims, No Drawings

HYDROPHILIC SEMIPERMEABLE MEMBRANES BASED ON COPOLYMERS OF ACRYLONITRILE AND HYDROXYALKYL ESTERS OF (METH) ACRYLIC ACID

BACKGROUND OF THE INVENTION

Ultrafiltration and/or dialysis membranes are barriers which permit selective transport of solvent and some solutes across them. They are used in a variety of industrial applications, ranging from the re-concentration of dilute paint dispersions to the isolation of food products and pharmaceuticals, and in biomedical applications such as hemodialysis. Such membranes are typically produced in three general physical formats: sheet membranes, hollow fibers, and tubes. Most permselective membrane disclosed in the literature are produced by solution/coagulation processes wherein a solubilized polymer is cast as a thin film and then coagulated in a non-solvent liquid. The non-solvent is generally selected from one of many liquids which is miscible with the solvent, but which reduces its solvent power, causing loss of polymer solubility when added to the solvent. Various adjuvants may also be added, either to the polymer solution and/or the coagulation bath, for example, to aid in control of the morphology of the resulting membrane.

Polymers which have found wide applicability as starting materials for membrane manufacture are roughly divisible into three categories. First, there are hydrogel polymers, such as cellulose, chitosan, and poly(vinylalcohol). These are characterized by high equilibrium water contents, large swelling values when cycled from dry to water wet states, and uniform cross-sectional structures. Second, there are glassy engineering plastics, such as poly(amides), poly(sulfones), poly(ethersulfones), poly(carbonates), and poly(dimethyl phenyleneoxides). These polymers are characterized by low equilibrium water contents and very strong hydrophobic bonding properties. They may or may not be semi-crystalline, as in the case of polyamides. Third, there are a number of vinyl copolymers, including copolymers of acrylonitrile (AN), or charged derivatives of engineering plastics, such as sulfonated poly(sulfone) (U.S. Pat. No. 4,207,182 to Marze) which exhibit some properties characteristics of each of the first two classes described. For example, a copolymer of acrylonitrile and methallylsulfonic acid used for hemodialysis (U.S. Pat. No. 4,545,910 to Marze) shows a significant equilibrium water content, approaching the values characteristic of hydrogels, but also has strong adsorptivity for human serum albumin (HSA) characteristic of the hydrophobic bonding properties encountered when the engineering plastics are used to prepare membranes. Alkyl copolymers of AN with alkyl(meth)acrylate esters are also known for textiles and membrane applications, but these are only marginally hydrophilic, with less than 15% equilibrium water content.

The preferred choice of polymer for a particular membrane application is governed by the anticipated application. A primary consideration is the mechanism of solute separation for the particular membrane which is based upon size fractionation of dissolved solutes. The porous structure of the membranes permit the selective transfer of molecules across them if the molecules are less than, for example, 0.5 times the diameter of the pore in size, and the pores are sized accordingly. However, because of the usual similarity of sizes between the pore dimensions and the effective hydrodynamic radii of the solutes in a typical membrane, multiple collisions occur between the solutes being separated and the walls of the membrane pores. As a consequence, the nature of the membrane material can also have a profound effect on the ability of solute molecules to pass through the membrane pores. Polymers with strong adsorption properties for the solute are affected in two ways: first, adsorbed molecules will restrict the pores, thus reducing the flux of solvent through the membranes. second, adsorption of solutes affects the sieving of other solutes trying to pass through the restricted pores. (See, e.g., Robertson, B.C. and Zidney, A.L. "Protein Adsorption in Asymmetric Membranes with Highly Constricted Pores" *J. Colloid and Interface Science* 134: 553–575 (1990))

These phenomena are particularly noticeable when protein solutions are processed to retain larger solutes via ultrafiltration or for dialytic removal of microsolutes. In both procedures the number and effective size of the membrane pore determines the efficiency of mass transfer. A number of scientific papers (See, e.g. "*Ultrafiltration Membranes and Applications*", A. R. Cooper, ed. Plenum Press, 1980) have demonstrated that the adsorption of proteins on the surfaces of pores in membranes made from hydrophobic polymers is the principal source of flux reduction through a mechanism termed "fouling". This mechanism is distinct from the loss of solvent flux through solute accumulation at the membrane surface via concentration polarization effects; the latter may operate even when there is no solute adsorption leading to "fouling".

DESCRIPTION OF RELATED ART

A number of attempts have been made to reduce membrane fouling resulting from solute adsorption. Since hydrogels made from hydrophilic polymers, such as cellulose, exhibit lower degrees of fouling, previous attempts have been directed to producing polymers which are more hydrophilic. When poly(sulfone) is the structural polymer, sulfonation has been used to increase hydrophilicity. AN copolymers have been of particular interest for membrane applications, since copolymers containing more than about 90% (w/w) are generally good film formers, have good stability in several polar solvents, and are resistant to bacteria; however, efforts to improve hydrophilicity of these copolymers have been directed to producing copolymers with charged monomers, such as dimethylaminoethylacrylate (Muir, U.S. Pat. No. 3,616,930), acrylic acid (Kim, J. H. and Kim, K. Y., Pollimo, 11, 71–80 (1987)), methallylsulfonic acid (Marze U.S. Pat. No. 4,545,910), and a variety of other charged co-monomers.

These attempts have been successful in only limited applications. While it is true that incorporating certain charged co-monomers into AN copolymers produces membranes which are more hydrophilic than membranes produced from AN copolymers incorporating neutral co-monomers, such as ethyl acrylate, methylmethacrylate (Levet et al *Blood Purif.* 4, 185–93 (1986)), methyl acrylate, vinyl chloride, ethylmethacrylate, and vinyl acetate, the presence of the charge site creates a new set of problems. In the filtration of proteins one can expect to encounter proteins with both positive and negative net charges at the pH where the separations must often be carried out. Human serum albumin at physiological pH is negatively charged. Immunoglobulins may be either negatively or positively charged at this pH. A number of marine and plant proteins are positively charged at this pH. More importantly, proteins contain segments along their lengths which may have local net charges, even when the overall charge on the protein is near zero. Charged segments of proteins can undergo local adsorption as a result of oppositely charged surfaces on the filtration membrane. Thus, separations using charged membranes risk the problem of protein adsorption by ion exchange mechanisms, even when the net charge of the target molecule is near zero. When such membranes are used in contact with blood, another disadvantage becomes apparent; a number of proteins effective in the human host defense processes are either activated and/or extracted by charged sites on such polymers.

SUMMARY OF THE INVENTION

The invention comprises highly hydrophilic, substantially uncharged porous semi-permeable membranes based on copolymers of acrylonitrile and hydroxy-$C_2$–$C_4$ alkyl esters of (meth)acrylic acid, preferably in flat sheet or hollow fiber form, and methods for the preparation of these membranes. As used herein, the term "(meth)acrylic acid" or "(meth)acrylate" refers interchangeably to methacrylic and acrylic acid or methacrylate and acrylate, respectively. The membranes do not have the disadvantage associated with those incorporating charged co-monomers, as described above, but still provide for high equilibrium water content. The membranes retain effective processability and bacterial resistance of known AN copolymers, and can be processed to obtain desired morphological membrane characteristics according to known principles applicable to AN copolymers of similar AN content.

DETAILED DESCRIPTION OF THE INVENTION

1. Preparation of the copolymers

The copolymers are prepared by copolymerizing a mixture of AN and hydroxy-$C_2$-$C_4$-alkyl (meth)acrylate ester monomers, free of more than about 0.1% of diacrylate ester, using for example standard redox and/or free radical catalysis mechanisms described in the literature, either in solvents or as aqueous dispersions (See, e.g. U.S. Pat. No. 2,436,926 incorporated herein by reference). In the examples below, aqueous dispersions were used; the invention is, however, not limited to copolymers prepared by this route. The choice of the particular hydroxyalkyl(meth)acrylate ester to be used is a function of the membrane properties desired in the end product. Membranes containing copolymers of acrylonitrile and hydroxyalkyl (meth)acrylate, especially hydroxyethyl acrylate, hydroxypropyl acrylate or hydroxybutyl acrylate, having high degrees of hyrophilicity are obtained when the acrylate co-monomer content is less than about 25% (w/w), preferably from about 3–20% (w/w), based on the weight of the copolymer. Since homopolymers of hydroxyalkyl esters of acrylic and methacrylic acid produce water soluble polymers, unless cross-linked with the corresponding dialkyl esters, and even when so cross-linked have extremely low wet strength and contain less than 50% water at equilibrium, it is unexpected that copolymers of AN and hydroxy-$C_2$-$C_4$-alkyl (meth)acrylates containing up to about 25 percent of hydroxy-$C_2$-$C_4$-alkyl esters of (meth)acrylic acid as described herein typically exhibit equilibrium water contents of more than 50% by weight and that these copolymers—despite their hydrophilicity—are easily soluble in a variety of organic solvents such as in dimethylformamide (DMF), dimethylacetamide (DMA), dimethylsulfoxide (DMSO) and N-methylpyrrolidinone (NMP), but are essentially insoluble in water, permitting the formation of asymmetric, permselective membranes by simple solution/coagulation mechanisms well known in the art for forming permselective membranes and their use with aqueous fluids. The water content is attributable to hydration of the copolymer (a chemical effect) rather than to capillary binding of water (a physical effect). Individual copolymers within the scope of the invention have characteristics which make them desirable for certain applications for protein separations, including hemodialysis. Because of their low adsorptivity for proteins, as shown below, these polymers are contemplated to be useful in applications where previous membranes have not been suitable. For example, in the processing of protein solutions such as milk whey by ultrafiltration, the reduced protein adsorption of the present membranes reduces flux loss. In the processing of human blood, the reduced interaction of these membranes with serum proteins leads to reduced complement activation. When used to immobilize enzymes, the absence of strong hydrophobic adsorption of these membranes tends to avoid enzyme denaturation. The observed absence of significant polymer-protein interaction of these membranes, presumably attributable to the high level of co-polymer hydration, provides membranes which exhibit only minimal deleterious effects when exposed to protein solutions.

2. Preparation of the permselective membranes

The membranes of the invention are produced from these novel AN/hydroxyalkyl (meth)acrylate ester copolymers by phase inversion mechanisms well known in the art of membrane manufacture ("The Use of Solubility Parameters for Solvent Selection in Asymmetric Membrane Formation" pgs. 61–83 in *Reverse Osmosis Research* H. K. Lonsdale and H. E. Podal, eds. Plenum Press, N.Y., N.Y. 1972 incorporated herein by references). In general, as is known in the art, a solution of copolymer is cast on a substrate, followed by quenching with a coagulation solution (i.e., a solution in which the copolymers is sparingly soluble or essentially insoluble) to form the permselective membrane. According to the present invention, the AN copolymers are dissolved in a polar organic solvent in which they are very soluble, preferably a solvent providing a copolymer solution containing no more than about 30% solids, and preferably no more than 25% solids. DMF, DMSO, NMP and DMA are exemplary. The copolymer solution is then cast on a suitable substrate, or extruded in the case of hollow fibers, and quenched with a coagulation solution to form the membrane. Suitable coagulation solutions for the purposes of the invention are aqueous solutions of water-miscible organic solvents which effectively coagulate the polymer to form a permselective membrane. Aqueous solutions of $C_1$-$C_4$ alkanols, DMF, and NMP are exemplary; in general, coagulation solutions containing $C_1$-$C_4$ alkanols are preferred for applications where the membrane is to be sterilized over DMF or NMP coagulation solutions, as membranes prepared with the latter are prone to collapse during autoclaving, whereas membranes coagulated with aqueous alcohol solutions, such as i-PrOH solutions, as described are stable to autoclaving. The membranes have excellent flux, up to about 300 ml/m²-hr-mm Hg. Preferred membranes have ultrafiltration rates of at least 1 ml/m²-hr-mm Hg most especially at least about 100 ml/m²-hr-mm Hg.

A surprising finding of this invention is that the selection of solvent and coagulants employed to prepare the membranes permits the formation of membranes with widely different mass transfer properties from the same starting polymer. Thus, coagulation of the copolymers from NMP solutions yields membranes with very large pore sizes, whose ultrafiltration coefficients are not strongly influenced by the NMP content of the coagulation bath. By contrast, the same copolymer dissolved in DMF solutions and coagulated by varying water/isopropanol (i-PrOH) mixtures permits formation of membranes with ultrafiltration coefficients (UFCs) differing by orders of magnitude, for example three orders of magnitude. Despite the wide range of attainable UFC, membranes coagulated with i-PrOH/water mixtures are found to be retentive to relatively small protein molecules such as BSA (bovine serum albumin), while membranes coagulated with DMF are at least retentive to relatively large protein molecules, such as IgM, for example, and in some instances are also retentive of smaller molecules. All membranes have reduced protein adsorption (fouling) and membranes coagulated with $C_1-C_4$ alkanols have particularly low protein adsorption. The membranes can thus be tailored for particular applications.

EXAMPLES

Methods and Materials a) Ultrafiltration Coefficient

A stirred ultrafiltration cell (Amicon model 8050 Amicon Inc., Danvers, MA.) was used measure the ultrafiltration coefficient and membrane sieving. Ultrafiltration coefficient measurements were made using water as test solution. The volumetric flux was measured in triplicate using a graduated 1-ml pipet, with five different applied pressure gradients. The ultrafiltration coefficient was calculated from the slope of a plot of volumetric flux versus pressure.

b) Water content

The water content of copolymers was determined by allowing the film to swell in water, removing excess water by gentle blotting, weighing the water swollen films, drying them at least 12 hours under vacuum, and reweighing. Similarly, the equilibrium water content of the powdered copolymers were obtained by equilibrating the powders in distilled water, centrifuging the wet powder at high speeds to remove surface and interstitial water, and then weighing the wet powder before and after drying.

c) Sieving coefficients for BSA

1% (by weight) of BSA (Sigma Chemical, St. Louis, MO.) in phosphate buffer (pH=7.4) was used as test solution to measure sieving coefficient. Sufficient pressure was applied on the test solution to produce a filtrate flux of approximately $1.0 \times 10^{-4}$ cm/sec. BSA concentrations in the filtrate and filtered solutions were measured using high pressure liquid chromatography with ultraviolet detection at 280 nm.

d) Absence of adsorbed protein effect

The membrane samples were exposed to 1% BSA solution for 5 minutes and then rinsed with distilled water. Then ultrafiltration coefficient was measured as described previously, and compared to the UFC value before protein exposure.

e) Resistance to autoclaving

The following methods were used to find the optimum conditions to autoclave the membranes.
 (i) treated with 100° C. water bath for 15 minutes; or
 (ii) autoclaved in water for 15 minutes in partially closed container; or
 (iii) first immersed in 40% glycerine/water for 20 minutes, removed excess water by gentle blotting, and autoclaved 15 minutes; or
 (iv) first immersed in 40% glycerine/water for 20 minutes and autoclaved in same solution for 15 minutes,
 (v) first immersed in 100% glycerine for 20 minutes, removed excess glycerine by gentle blotting, and autoclaved for 15 minutes,
 (vi) first immersed in 100% glycerine for 20 minutes and autoclaved in same solution for 15 minutes. The minimum shrinkage was obtained from method (v) and this procedure was used to autoclave all membranes.

EXAMPLE 1

Polymerization

Aqueous copolymerization of 95 parts of acrylonitrile and either 5 parts of 2-hydroxyethyl acrylate or 5 parts of 4-hydroxybutyl acrylate at room temperature was carried out as follows: A solution consisting of 2700 parts of water and 7.35 parts of ammonium persulfate was placed in a glass kettle equipped with a stirrer, nitrogen inlet, and reflux condenser. Stirring was started and nitrogen was passed through for 30 minutes. The selected mixture of monomers together with sodium bisulfite (250 parts of 1% solution), was degassed and added to the reaction mixture during a period of half an hour. Polymerization commenced within a few minutes and the reaction was allowed to proceed at least three hours until complete. Stirring and a gentle current of nitrogen over the mixture was maintained during the polymerization. The precipitated copolymer was filtered off and washed with three liters of deionized water in order to remove unpolymerized monomers as well as catalyst. The resulting copolymer was dried under vacuum. The yield of copolymers after the working-up procedure amounted up to 90%. Solutions of the copolymers for use in Example 2 were obtained by dissolving the dried copolymer in solvent as described below.

EXAMPLE 2

Membrane casting

Membranes were prepared by casting a 150 μm thickness of copolymer solution on a glass plate at temperatures between 25° and 65° C. To prepare the casting solution, copolymer as obtained in Example 1, and solubilized as described below was placed in a bottle and stirred overnight at 65° C. and then centrifuged at 3000 rpm for one hour. The supernatant copolymer solution was used to cast the membranes as described below. The same procedure was used to obtain membranes under the following three conditions, using either of the copolymers.

a) From DMF into DMF/water

A solution of 18% (by weight) copolymer in DMF was cast on the glass plates, followed by coagulation of the polymer solution film in a water/DMF coagulation solution containing varying amounts of water (Table 2). The resulting membrane was washed with deionized water for one hour after quenching with the coagulation bath for approximately 20 minutes. Then membranes were stored in 0.02% azide in physiological saline solution.

b) From DMF into i-PrOH/water

A solution of 15% (by weight) of copolymer in DMF was used to cast membranes using the above procedure and quenched in a coagulation solution of water/i-ProH containing varying amounts of water (Table 1). Membranes were stored as described.

c) From NMP into NMP/water

A solution of 15% (by weight) of copolymer in NMP was used to cast membranes using the above procedure and quenched in a coagulation solution of water/NMP containing varying amount of water (Table 3). The membranes were stored as described.

EXAMPLE 3

UFC Before and After Autoclaving

The properties of the membranes obtained in Example 2 are tabulated below, together with the composition of the casting solution and the coagulation bath composition. To illustrate the effects of i-PrOH content in the coagulation solution, the UFC of the membrane is shown before and after autoclaving, for a membrane made from AN:HEA (hydroxyethylacrylate) copolymer cast from a 15% (w/w) solution in DMF

TABLE 1

Ultrafiltration Coefficient (UFC) of AN:HEA Copolymers before and after autoclaving.

| Sample | % Water in i-PrOH | UFC (ml/hr-m$^2$-mm Hg) before Autoclave | After Autoclave |
|---|---|---|---|
| NBP 90a | 10 | 0.0178 | 0.0274 |
| NBP 90b | 15 | 0.072 | 0.1872 |
| NBP 90d | 25 | 87.89 | 56.304 |
| NBP 90e | 30 | 109.44 | 73.200 |

The data illustrate that with this combination of casting solution/coagulation solution membranes are produced which lose less than 40% of their initial water flux during sterilizing steam treatment. This is a surprising result in view of the fact that the following table, showing data with the same polymer cast into a DMF/water coagulant solution, loses almost all flux as a result of autoclaving.

TABLE 2

Ultrafiltration Coefficient (UFC) of AN:HEA Copolymers before and after autoclaving.

| Sample | % Water in DMF | UFC (ml/hr-m$^2$-mm Hg) before Autoclave | After Autoclave |
|---|---|---|---|
| NBP 44a | 40 | 96.96 | 4.32 |
| NBP 44b | 50 | 67.68 | 1.48 |
| NBP 44c | 60 | 78.72 | 0.80 |
| NBP 44e | 80 | 81.60 | 0.40 |
| NBP 44f | 100 | 103.68 | 2.08 |

Concentration: 18% (w/w) in DMF

This is further confirmed by the results of Table 3 showing that casting the same polymer dissolved in NMP into a mixture of NMP/water also leads to the loss of flux following autoclaving.

TABLE 3

Ultrafiltration Coefficient (UFC) of AN:HEA Copolymers before and after autoclaving.

| Sample | % Water in NMP | UFC (ml/hr-m$^2$-mm Hg) before Autoclave | After Autoclave |
|---|---|---|---|
| NBP 45a | 40 | 172.8 | 74.4 |
| NBP 45b | 50 | 259.2 | 81.5 |
| NBP 45c | 60 | 241.4 | 8.4 |
| NBP 45d | 70 | 302.4 | 31.9 |
| NBP 45e | 80 | 323.0 | 59.3 |

Concentration: 15% (w/w) in NMP

The use of an i-PrOH water coagulation bath, when combined with film formation of the AN:hydroxyalkyl (meth)acrylate copolymers leads to membranes with unexpected thermal stability. Moreover, the use of this combination of copolymer/solvent/coagulation system permits the preparation of semi-permeable membranes whose ultrafiltration coefficients can be varied over a range of more than 2,000X.

The hydrophilic properties of the membranes produced from the described polymers are exemplified by the small interaction between bovine serum albumin and the membrane matrix, as evidenced by small reductions of UFC following BSA exposures, as described previously. Even those solution/coagulation conditions which lead to very highly permeable membranes (implying very high internal surface areas) are not greatly affected by BSA exposure. This is seen in Table 4 with AN:HEA membranes prepared in NMP and coagulated with NMP/water mixtures, as described in example 2.

TABLE 4

Ultrafiltration Coefficient (UFC) of AN:HEA Copolymers before and after BSA exposure.

| Sample | % Water in NMP | UFC (ml/hr-m$^2$-mm Hg) Before | After |
|---|---|---|---|
| NBP 45a | 40 | 172.8 | 161.8 |
| NBP 45b | 50 | 259.2 | 209.8 |
| NBP 45c | 60 | 241.4 | 204.9 |
| NBP 45d | 70 | 302.4 | 225.1 |
| NBP 45e | 80 | 323.0 | 235.7 |

Concentration: 15% (w/w) in NMP

Lesser effects are seen when the same test is conducted with AN:HEA membranes prepared to have lower UFCs, as is shown in Table 5 for solutions prepared from DMF and coagulated in mixtures of i-PrOH/water, as described in Example 2

TABLE 5

Ultrafiltration Coefficient (UFC) of AN:HEA Copolymers before and after BSA exposure

| Sample | % Water in i-PrOH | UFC (ml/hr-m$^2$-mm Hg) Before | After |
|---|---|---|---|
| NBP 90b | 15 | 0.072 | 0.082 |
| NBP 90c | 20 | 22.40 | 21.98 |

TABLE 5-continued

Ultrafiltration Coefficient (UFC) of AN:HEA Copolymers before and after BSA exposure

| Sample | % Water in i-PrOH | UFC (ml/hr-m²-mm Hg) Before | After |
|---|---|---|---|
| NBP 90d | 25 | 145.0 | 129.0 |
| NBP 90e | 30 | 192.0 | 153.6 |

Concentration: 15% (w/w) in DMF

This particular combination of solution/coagulant conditions (which produced autoclave stable membranes) allows a great deal of control over the UFCs obtained simply by control of the water content of the i-PrOH/water mixture. Sample 90b has a permeability characteristic of nanofiltration membranes; i.e. it permits free flow of solvent and low molecular weight salts, but retains approximately 50% of glucose concentrations filtered through it. But sample 90e has a UFC characteristic of high flux ultrafilters.

The same absence of BSA response, shown in Table 6, is seen with the hydroxybutylacrylate co-monomer, in a membrane according to Example 2, as was seen with the hydroxyethylacrylate co-monomer of Table 5. Furthermore, it is a property of the copolymers, as shown by the similarity of responses in tables 6 and 7, where different coagulation solutions are used.

TABLE 6

Ultrafiltration Coefficient (UFC) of AN:HBA Copolymers before and after BSA exposure. (DMF into i-PrOH/water)

| Sample | % Water in i-PrOH | UFO (ml/hr-m²-mm Hg) Before | After |
|---|---|---|---|
| NBP 17a | 10 | 0.072 | 0.067 |
| NBP 17b | 15 | 10.20 | 9.936 |
| NBP 17c | 20 | 85.78 | 79.15 |
| NBP 17d | 25 | 147.36 | 139.20 |
| NBP 17e | 30 | 170.50 | 156.62 |

Concentration: 15% (w/w) in DMF

TABLE 7

Ultrafiltration Coefficient of AN:HBA Copolymers before and after BSA exposure. (DMF into DMF/water)

| Sample | % Water in DMF | Ultrafiltration Coefficient (ml/hr. m²) Before | After |
|---|---|---|---|
| NBP 44a | 40 | 96.96 | 82.32 |
| NBP 44b | 50 | 67.68 | 64.80 |
| NBP 44c | 60 | 78.72 | 69.12 |
| NBP 44e | 80 | 81.60 | 74.88 |
| NBP 44f | 100 | 103.68 | 86.88 |

Concentration: 18% (w/w) in DMF

4. Sieving

The sieving properties of the membranes described here are important operational variables in their use. To characterize their performance the sieving of a 66,000 dalton protein bovine serum albumin is reported below, which is typical of many proteins encountered in various fluid processing applications. The membranes made by the described procedures may be asymmetric, as deduced from the fact that they retain BSA completely (sieving <5%) despite a wide variation in UFC when coagulated with the i-PrOH/water system. When the coagulation was carried out in a preferred coagulant, i-PrOH, the results shown in Table 8 were attained:

TABLE 8

Sieving properties of Acrylonitrile-co- 2 Hydroxyethyl acrylate membrane (Example 2)

| Copolymer (95:5) (Conc.) | Percentage of water in Isopropanol | Ultrafiltration coefficient (ml/hr. m²mm Hg) | Sieving (%) AN:HEA, |
|---|---|---|---|
| NBP90a 14.4% (w/w) | 10 | 0.0178 | 0.00 |
| AN:HEA, NBP90b 14.4% (w/w) | 15 | 3.744 | 0.22 |
| AN:HEA, NBP90c 14.4% (w/w) | 20 | 15.36 | 0.17 |
| AN:HEA, NBP90d 14.4% (w/w) | 25 | 87.89 | 0.16 |
| AN:HEA, NBP90e 14.4% (w/w) | 30 | 109.4 | 0.37 |

However, when the NMP solvent system was used—which leads to very high UFCs—permeability to BSA was achieved, as shown in Table 9:

TABLE 9

Sieving properties of Acrylonitrile-co- 2 Hydroxyethyl acrylate membrane

| Copolymer (95:5) (Conc.) | Percentage of water in NMP | Ultrafiltration coefficient (ml/hr. m²mm Hg) | Sieving (%) HPLC |
|---|---|---|---|
| AN:HEA, NBP50 15.0% (w/w) | 40 | 171 | 21.0 |
| AN:HEA, NBP49 15.0% (w/w) | 50 | 223 | 49.0 |
| AN:HEA, NBP47 15.0% (w/w) | 70 | 275 | 53.0 |
| AN:HEA, NBP46 15.0% (w/w) | 80 | 268 | 59.0 |

Membranes prepared with the NMP solvent and NMP/water coagulation system permit partial permeation of BSA but not of larger proteins, such as IgA.

When the copolymers were dissolved in DMF and coagulated in mixtures of that solvent and water (Example 2), the resulting membranes were fully retentive of BSA, as exemplified in Table 10, for the hydroxyethyl copolymer, and in Table 11 for the hydroxybutyl copolymer:

TABLE 10

Sieving properties of Acrylonitrile-co- 2 Hydroxyethyl acrylate membrane

| Copolymer (95:5) (Conc.) | Percentage of water in DMF | Ultrafiltration coefficient (ml/hr. m²mm Hg) | Sieving (%) HPLC |
|---|---|---|---|
| AN:HEA, NBP62 18.0% (w/w) | 50 | 73.92 | 0.76 |
| AN:HEA, NBP63 18.0% (w/w) | 60 | 86.19 | 1.46 |
| AN:HEA, NBP37 18.0% (w/w) | 70 | 67.20 | 1.70 |
| AN:HEA, NBP64 18.0% (w/w) | 80 | 76.80 | 0.00 |
| AN:HEA, NBP65 18.0% (w/w) | 100 | 105.60 | 0.00 |

TABLE 11

Sieving properties of Acrylonitrile-co- 4 Hydroxybutylacrylate membrane

| Copolymer (95:5) (Conc.) | Percentage of water in DMF | Ultrafiltration coefficient (ml/hr. m²mm Hg) | Sieving (%) HPLC |
|---|---|---|---|
| AN:HBA, NBP53 18.0% (w/w) | 50 | 71.52 | 2.8 |
| AN:HBA, NBP54 | 60 | 64.80 | 0.2 |

TABLE 11-continued

| Copolymer (95:5) (Conc.) | Sieving properties of Acrylonitrile-co-4 Hydroxybutylacrylate membrane | | |
|---|---|---|---|
| | Percentage of water in DMF | Ultrafiltration coefficient (ml/hr. m²mm Hg) | Sieving (%) HPLC |
| 18.0% (w/w) AN:HBA, NBP55 | 70 | 79.20 | 0.3 |
| 18.0% (w/w) AN:HBA, NBP56 | 80 | 93.12 | 0.6 |
| 18.0% (w/w) | | | |

What is claimed is:

1. A semi-permeable hydrophilic membrane comprising a copolymer of acrylonitrile and a $C_2$-$C_4$ hydroxyalkyl ester of (meth)acrylic acid as comonomer, having an ultrafiltration rate of from about 1–300 (ml/hr.m²mm Hg).

2. The membrane of claim 1 having improved stability to autoclaving, reduced protein adsorption, and a pore size sufficiently small to retain at least IgM.

3. The membrane of claim 2, wherein the pore size is sufficiently small to retain at least BSA.

4. The membrane of claim 1, having an ultrafiltration rate of at least about 100 (ml/hr.m²mm Hg).

5. The membrane of claim 2, having an ultrafiltration rate of at least about 100 (ml/hr.m²mm Hg).

6. The membrane of claim 1, wherein the hydroxyalkyl ester comonomer is present in the copolymer in an amount up to about 25% (w/w) based on the weight of the copolymer.

7. The membrane of claim 4 wherein the hydroxyalkyl ester comonomer is present in the copolymer in an amount up to about 25% w/w of the copolymer.

8. The membrane of claim 7, wherein the comonomer is present in an amount of about 3–20% (w/w), based on the weight of the copolymer.

9. The membrane of claim 8 characterized by a substantial water regain at equilibrium.

10. The membrane of claim 8, characterized by a water content of greater than about 50% (w/w) based on the weight of the membrane at equilibrium with distilled water.

11. The membrane of claim 1, further characterized by an ultrafiltration rate of at least about 100 (ml/hr m²mm Hg) and a pore size at least sufficient to retain a molecule at least about 62,000 daltons.

12. The membrane of claim 1 which is substantially uncharged.

13. The membrane of claim 1, characterized by stability to autoclaving.

14. The membrane of claim 6 wherein the hydroxyalkyl ester is hydroxyethyl— or hydroxybutylacrylate.

15. The membrane of claim 8 wherein the hydroxyalkyl ester is hydroxyethyl— or hydroxybutylacrylate.

16. The membrane of claim 1, wherein the comonomer content of the copolymer is from 3 to 20% by weight of the copolymer.

17. The membrane of claim 16, wherein the comonomer is an hydroxyethyl or hydroxybutyl ester of acrylic acid.

18. A method for the ultrafiltration or dialysis of a biological fluid comprising filtering the fluid through the semi-permeable membrane of claim 8.

19. The method of claim 18 wherein the biological fluid is blood.

20. The membrane of claim 1 in the form of a sheet or a hollow fiber.

21. The membrane of claim 16, characterized by reduced protein adsorption.

22. The method of claim 18, wherein the membrane is further characterized by a water content of greater than about 50% (w/w) based on the weight of the membrane at equilibrium with distilled water.

* * * * *